United States Patent
de la Motte et al.

(10) Patent No.: US 10,653,714 B2
(45) Date of Patent: May 19, 2020

(54) COMPOSITION AND METHOD TO ENHANCE EXPRESSION OF HUMAN DEFENSIN 2

(71) Applicant: THE CLEVELAND CLINIC FOUNDATION, Cleveland, OH (US)

(72) Inventors: Carol de la Motte, Broadview Heights, OH (US); Sean Kessler, Rocky River, OH (US); David Richard Hill, Ypsilanti, MI (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 15/798,848

(22) Filed: Oct. 31, 2017

(65) Prior Publication Data

US 2018/0117078 A1    May 3, 2018

Related U.S. Application Data

(62) Division of application No. 14/115,181, filed as application No. PCT/US2012/036936 on May 8, 2012.

(60) Provisional application No. 61/609,657, filed on Mar. 12, 2012, provisional application No. 61/484,044, filed on May 9, 2011.

(51) Int. Cl.
| | | |
|---|---|---|
| *A61K 31/728* | (2006.01) | |
| *A23L 33/10* | (2016.01) | |
| *A23L 33/19* | (2016.01) | |
| *A61K 47/61* | (2017.01) | |
| *A61K 47/64* | (2017.01) | |
| *A61K 38/40* | (2006.01) | |
| *A61K 9/127* | (2006.01) | |

(52) U.S. Cl.
CPC ............ *A61K 31/728* (2013.01); *A23L 33/10* (2016.08); *A23L 33/19* (2016.08); *A61K 9/127* (2013.01); *A61K 38/40* (2013.01); *A61K 47/61* (2017.08); *A61K 47/644* (2017.08)

(58) Field of Classification Search
None
See application file for complete search history.

(56) References Cited

U.S. PATENT DOCUMENTS

| 6,537,978 B1 | 3/2003 | Turley et al. |
| 6,803,031 B2 | 10/2004 | Rabinowitz et al. |
| 2005/0043270 A1 | 2/2005 | Kono et al. |
| 2007/0142292 A1 | 6/2007 | Varadhachary et al. |
| 2010/0074870 A1 | 3/2010 | Russell et al. |

FOREIGN PATENT DOCUMENTS

| WO | WO 2007145520 | 12/2007 |
| WO | WO 2010081800 | 7/2010 |

OTHER PUBLICATIONS

PCT Search Report and Written Opinion for PCT/US2012/036936, completed Jun. 12, 2012.
Alauzun, Johan G., et al., "Biocompatible, Hyaluronic Acid Modified Silicone Elastomers", 2010, Biomaterials, No. 31, pp. 3471-3478.
Jing, Wei, et al., "Synchronized Chemoenzymatic Synthesis of Monodisperse Hyaluronan Polymers", 2004, The Journal of Biological Chemistry, vol. 279, No. 40, pp. 42345-42349.
De La Motte, Carol, et al., "Platelet-Derived Hyaluronidase 2 Cleaves Hyaluronan into Fragments that Trigger Monocyte-Mediated Production of Proinflammatory Cytokines", 2009, The American Journal of Pathology, vol. 174, No. 6, pp. 2254-2264.

*Primary Examiner* — Dennis J Parad
(74) *Attorney, Agent, or Firm* — Barnes & Thornburg LLP

(57) ABSTRACT

Compositions and methods are provided for enhancing the expression of human beta defensin 2 (HBD2) in human colon epithelium cells. The method comprises orally administering a composition comprising hyaluronan, where said hyaluronan has a molecular weight within the range of about 35 kDa.

5 Claims, 6 Drawing Sheets

Specification includes a Sequence Listing.

N=12. Statistical significance evaluated by comparison of experimental groups to Medium treatment alone using one-tailed Student's T-test. 'N.S.' indicates no significant increase in expression relative to control, while '' and '*' indicate $P < 0.01$ or $P < 0.001$ respectively.

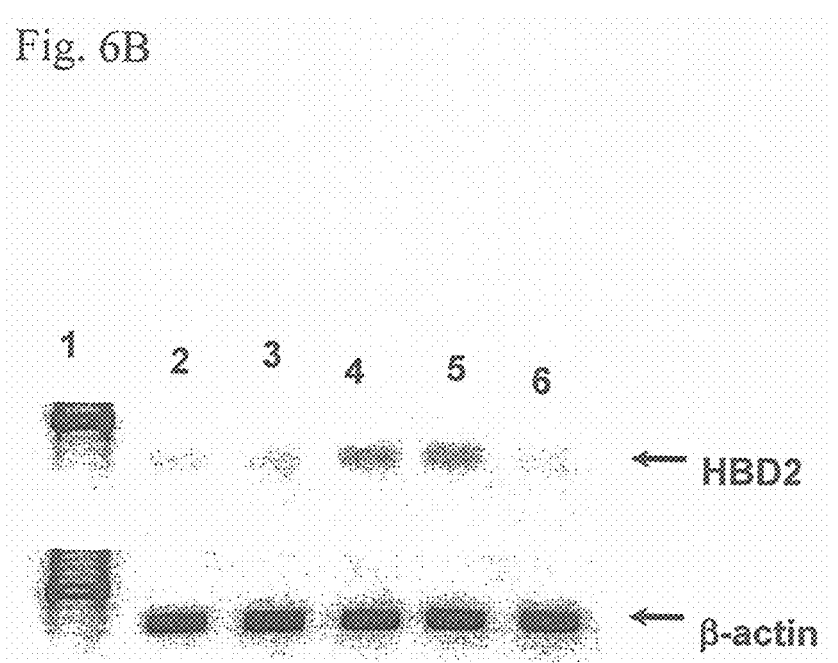

SEQUENCE LISTING

```
<160> NUMBER OF SEQ ID NOS: 4

<210> SEQ ID NO 1
<211> LENGTH: 710
<212> TYPE: PRT
<213> ORGANISM: Homo sapiens

<400> SEQUENCE: 1

Met Lys Leu Val Phe Leu Val Leu Leu Phe Leu Gly Ala Leu Gly Leu
1               5                   10                  15

Cys Leu Ala Gly Arg Arg Ser Val Gln Trp Cys Ala Val Ser Gln
            20                  25                  30

Pro Glu Ala Thr Lys Cys Phe Gln Trp Gln Arg Asn Met Arg Lys Val
            35                  40                  45

Arg Gly Pro Pro Val Ser Cys Ile Lys Arg Asp Ser Pro Ile Gln Cys
        50                  55                  60

Ile Gln Ala Ile Ala Glu Asn Arg Ala Asp Ala Val Thr Leu Asp Gly
65                  70                  75                  80

Gly Phe Ile Tyr Glu Ala Gly Leu Ala Pro Tyr Lys Leu Arg Pro Val
                85                  90                  95

Ala Ala Glu Val Tyr Gly Thr Glu Arg Gln Pro Arg Thr His Tyr Tyr
            100                 105                 110

Ala Val Ala Val Val Lys Lys Gly Gly Ser Phe Gln Leu Asn Glu Leu
        115                 120                 125

Gln Gly Leu Lys Ser Cys His Thr Gly Leu Arg Arg Thr Ala Gly Trp
    130                 135                 140

Asn Val Pro Ile Gly Thr Leu Arg Pro Phe Leu Asn Trp Thr Gly Pro
145                 150                 155                 160

Pro Glu Pro Ile Glu Ala Ala Val Ala Arg Phe Phe Ser Ala Ser Cys
                165                 170                 175

Val Pro Gly Ala Asp Lys Gly Gln Phe Pro Asn Leu Cys Arg Leu Cys
            180                 185                 190

Ala Gly Thr Gly Glu Asn Lys Cys Ala Phe Ser Ser Gln Glu Pro Tyr
        195                 200                 205

Phe Ser Tyr Ser Gly Ala Phe Lys Cys Leu Arg Asp Gly Ala Gly Asp
    210                 215                 220
```

-continued

Val Ala Phe Ile Arg Glu Ser Thr Val Phe Glu Asp Leu Ser Asp Glu
225                 230                 235                 240

Ala Glu Arg Asp Glu Tyr Glu Leu Leu Cys Pro Asp Asn Thr Arg Lys
            245                 250                 255

Pro Val Asp Lys Phe Lys Asp Cys His Leu Ala Arg Val Pro Ser His
        260                 265                 270

Ala Val Val Ala Arg Ser Val Asn Gly Lys Glu Asp Ala Ile Trp Asn
    275                 280                 285

Leu Leu Arg Gln Ala Gln Glu Lys Phe Gly Lys Asp Lys Ser Pro Lys
290                 295                 300

Phe Gln Leu Phe Gly Ser Pro Ser Gly Gln Lys Asp Leu Leu Phe Lys
305                 310                 315                 320

Asp Ser Ala Ile Gly Phe Ser Arg Val Pro Pro Arg Ile Asp Ser Gly
            325                 330                 335

Leu Tyr Leu Gly Ser Gly Tyr Phe Thr Ala Ile Gln Asn Leu Arg Lys
        340                 345                 350

Ser Glu Glu Glu Val Ala Ala Arg Arg Ala Arg Val Val Trp Cys Ala
    355                 360                 365

Val Gly Glu Gln Glu Leu Arg Lys Cys Asn Gln Trp Ser Gly Leu Ser
370                 375                 380

Glu Gly Ser Val Thr Cys Ser Ser Ala Ser Thr Thr Glu Asp Cys Ile
385                 390                 395                 400

Ala Leu Val Leu Lys Gly Glu Ala Asp Ala Met Ser Leu Asp Gly Gly
            405                 410                 415

Tyr Val Tyr Thr Ala Gly Lys Cys Gly Leu Val Pro Val Leu Ala Glu
        420                 425                 430

Asn Tyr Lys Ser Gln Gln Ser Ser Asp Pro Asp Pro Asn Cys Val Asp
    435                 440                 445

Arg Pro Val Glu Gly Tyr Leu Ala Val Ala Val Val Arg Arg Ser Asp
450                 455                 460

Thr Ser Leu Thr Trp Asn Ser Val Lys Gly Lys Lys Ser Cys His Thr
465                 470                 475                 480

Ala Val Asp Arg Thr Ala Gly Trp Asn Ile Pro Met Gly Leu Leu Phe
            485                 490                 495

Asn Gln Thr Gly Ser Cys Lys Phe Asp Glu Tyr Phe Ser Gln Ser Cys
        500                 505                 510

Ala Pro Gly Ser Asp Pro Arg Ser Asn Leu Cys Ala Leu Cys Ile Gly
    515                 520                 525

Asp Glu Gln Gly Glu Asn Lys Cys Val Pro Asn Ser Asn Glu Arg Tyr
530                 535                 540

Tyr Gly Tyr Thr Gly Ala Phe Arg Cys Leu Ala Glu Asn Ala Gly Asp
545                 550                 555                 560

Val Ala Phe Val Lys Asp Val Thr Val Leu Gln Asn Thr Asp Gly Asn
            565                 570                 575

Asn Asn Glu Ala Trp Ala Lys Asp Leu Lys Leu Ala Asp Phe Ala Leu
        580                 585                 590

Leu Cys Leu Asp Gly Lys Arg Lys Pro Val Thr Glu Ala Arg Ser Cys
    595                 600                 605

His Leu Ala Met Ala Pro Asn His Ala Val Val Ser Arg Met Asp Lys
610                 615                 620

Val Glu Arg Leu Lys Gln Val Leu Leu His Gln Gln Ala Lys Phe Gly
625                 630                 635                 640

Arg Asn Gly Ser Asp Cys Pro Asp Lys Phe Cys Leu Phe Gln Ser Glu

```
                    645                 650                 655
Thr Lys Asn Leu Leu Phe Asn Asp Asn Thr Glu Cys Leu Ala Arg Leu
            660                 665                 670

His Gly Lys Thr Thr Tyr Glu Lys Tyr Leu Gly Pro Gln Tyr Val Ala
            675                 680                 685

Gly Ile Thr Asn Leu Lys Lys Cys Ser Thr Ser Pro Leu Leu Glu Ala
            690                 695                 700

Cys Glu Phe Leu Arg Lys
705                 710

<210> SEQ ID NO 2
<211> LENGTH: 691
<212> TYPE: PRT
<213> ORGANISM: Homo sapiens

<400> SEQUENCE: 2

Gly Arg Arg Arg Ser Val Gln Trp Cys Ala Val Ser Gln Pro Glu Ala
1               5                   10                  15

Thr Lys Cys Phe Gln Trp Gln Arg Asn Met Arg Lys Val Arg Gly Pro
            20                  25                  30

Pro Val Ser Cys Ile Lys Arg Asp Ser Pro Ile Gln Cys Ile Gln Ala
        35                  40                  45

Ile Ala Glu Asn Arg Ala Asp Ala Val Thr Leu Asp Gly Gly Phe Ile
50                  55                  60

Tyr Glu Ala Gly Leu Ala Pro Tyr Lys Leu Arg Pro Val Ala Ala Glu
65                  70                  75                  80

Val Tyr Gly Thr Glu Arg Gln Pro Arg Thr His Tyr Tyr Ala Val Ala
                85                  90                  95

Val Val Lys Lys Gly Gly Ser Phe Gln Leu Asn Glu Leu Gln Gly Leu
            100                 105                 110

Lys Ser Cys His Thr Gly Leu Arg Arg Thr Ala Gly Trp Asn Val Pro
        115                 120                 125

Ile Gly Thr Leu Arg Pro Phe Leu Asn Trp Thr Gly Pro Pro Glu Pro
130                 135                 140

Ile Glu Ala Ala Val Ala Arg Phe Phe Ser Ala Ser Cys Val Pro Gly
145                 150                 155                 160

Ala Asp Lys Gly Gln Phe Pro Asn Leu Cys Arg Leu Cys Ala Gly Thr
                165                 170                 175

Gly Glu Asn Lys Cys Ala Phe Ser Ser Gln Glu Pro Tyr Phe Ser Tyr
            180                 185                 190

Ser Gly Ala Phe Lys Cys Leu Arg Asp Gly Ala Gly Asp Val Ala Phe
        195                 200                 205

Ile Arg Glu Ser Thr Val Phe Glu Asp Leu Ser Asp Glu Ala Glu Arg
210                 215                 220

Asp Glu Tyr Glu Leu Leu Cys Pro Asp Asn Thr Arg Lys Pro Val Asp
225                 230                 235                 240

Lys Phe Lys Asp Cys His Leu Ala Arg Val Pro Ser His Ala Val Val
                245                 250                 255

Ala Arg Ser Val Asn Gly Lys Glu Asp Ala Ile Trp Asn Leu Leu Arg
            260                 265                 270

Gln Ala Gln Glu Lys Phe Gly Lys Asp Lys Ser Pro Lys Phe Gln Leu
        275                 280                 285

Phe Gly Ser Pro Ser Gly Gln Lys Asp Leu Leu Phe Lys Asp Ser Ala
    290                 295                 300
```

```
Ile Gly Phe Ser Arg Val Pro Pro Arg Ile Asp Ser Gly Leu Tyr Leu
305                 310                 315                 320

Gly Ser Gly Tyr Phe Thr Ala Ile Gln Asn Leu Arg Lys Ser Glu Glu
            325                 330                 335

Glu Val Ala Ala Arg Arg Ala Arg Val Val Trp Cys Ala Val Gly Glu
            340                 345                 350

Gln Glu Leu Arg Lys Cys Asn Gln Trp Ser Gly Leu Ser Glu Gly Ser
            355                 360                 365

Val Thr Cys Ser Ser Ala Ser Thr Thr Glu Asp Cys Ile Ala Leu Val
            370                 375                 380

Leu Lys Gly Glu Ala Asp Ala Met Ser Leu Asp Gly Gly Tyr Val Tyr
385                 390                 395                 400

Thr Ala Gly Lys Cys Gly Leu Val Pro Val Leu Ala Glu Asn Tyr Lys
                405                 410                 415

Ser Gln Gln Ser Ser Asp Pro Asp Pro Asn Cys Val Asp Arg Pro Val
            420                 425                 430

Glu Gly Tyr Leu Ala Val Ala Val Val Arg Arg Ser Asp Thr Ser Leu
            435                 440                 445

Thr Trp Asn Ser Val Lys Gly Lys Lys Ser Cys His Thr Ala Val Asp
450                 455                 460

Arg Thr Ala Gly Trp Asn Ile Pro Met Gly Leu Leu Phe Asn Gln Thr
465                 470                 475                 480

Gly Ser Cys Lys Phe Asp Glu Tyr Phe Ser Gln Ser Cys Ala Pro Gly
                485                 490                 495

Ser Asp Pro Arg Ser Asn Leu Cys Ala Leu Cys Ile Gly Asp Glu Gln
            500                 505                 510

Gly Glu Asn Lys Cys Val Pro Asn Ser Asn Glu Arg Tyr Tyr Gly Tyr
            515                 520                 525

Thr Gly Ala Phe Arg Cys Leu Ala Glu Asn Ala Gly Asp Val Ala Phe
            530                 535                 540

Val Lys Asp Val Thr Val Leu Gln Asn Thr Asp Gly Asn Asn Asn Glu
545                 550                 555                 560

Ala Trp Ala Lys Asp Leu Lys Leu Ala Asp Phe Ala Leu Leu Cys Leu
                565                 570                 575

Asp Gly Lys Arg Lys Pro Val Thr Glu Ala Arg Ser Cys His Leu Ala
            580                 585                 590

Met Ala Pro Asn His Ala Val Val Ser Arg Met Asp Lys Val Glu Arg
            595                 600                 605

Leu Lys Gln Val Leu Leu His Gln Gln Ala Lys Phe Gly Arg Asn Gly
            610                 615                 620

Ser Asp Cys Pro Asp Lys Phe Cys Leu Phe Gln Ser Glu Thr Lys Asn
625                 630                 635                 640

Leu Leu Phe Asn Asp Asn Thr Glu Cys Leu Ala Arg Leu His Gly Lys
                645                 650                 655

Thr Thr Tyr Glu Lys Tyr Leu Gly Pro Gln Tyr Val Ala Gly Ile Thr
            660                 665                 670

Asn Leu Lys Lys Cys Ser Thr Ser Pro Leu Leu Glu Ala Cys Glu Phe
            675                 680                 685

Leu Arg Lys
    690

<210> SEQ ID NO 3
<211> LENGTH: 707
<212> TYPE: PRT
```

<213> ORGANISM: Mus musculus

<400> SEQUENCE: 3

Met Arg Leu Leu Ile Pro Ser Leu Ile Phe Leu Glu Ala Leu Gly Leu
1               5                   10                  15

Cys Leu Ala Lys Ala Thr Thr Val Gln Trp Cys Ala Val Ser Asn Ser
            20                  25                  30

Glu Glu Glu Lys Cys Leu Arg Trp Gln Asn Glu Met Arg Lys Val Gly
        35                  40                  45

Gly Pro Pro Leu Ser Cys Val Lys Lys Ser Ser Thr Arg Gln Cys Ile
    50                  55                  60

Gln Ala Ile Val Thr Asn Arg Ala Asp Ala Met Thr Leu Asp Gly Gly
65                  70                  75                  80

Thr Met Phe Asp Ala Gly Lys Pro Pro Tyr Lys Leu Arg Pro Val Ala
                85                  90                  95

Ala Glu Val Tyr Gly Thr Lys Glu Gln Pro Arg Thr His Tyr Tyr Ala
            100                 105                 110

Val Ala Val Val Lys Asn Ser Ser Asn Phe His Leu Asn Gln Leu Gln
        115                 120                 125

Gly Leu Arg Ser Cys His Thr Gly Ile Gly Arg Ser Ala Gly Trp Lys
    130                 135                 140

Ile Pro Ile Gly Thr Leu Arg Pro Tyr Leu Asn Trp Asn Gly Pro Pro
145                 150                 155                 160

Ala Ser Leu Glu Glu Ala Val Ser Lys Phe Phe Ser Lys Ser Cys Val
                165                 170                 175

Pro Gly Ala Gln Lys Asp Arg Phe Pro Asn Leu Cys Ser Cys Ala
            180                 185                 190

Gly Thr Gly Ala Asn Lys Cys Ala Ser Ser Pro Glu Glu Pro Tyr Ser
    195                 200                 205

Gly Tyr Ala Gly Ala Leu Arg Cys Leu Arg Asp Asn Ala Gly Asp Val
    210                 215                 220

Ala Phe Thr Arg Gly Ser Thr Val Phe Glu Glu Leu Pro Asn Lys Ala
225                 230                 235                 240

Glu Arg Asp Gln Tyr Lys Leu Leu Cys Pro Asp Asn Thr Trp Lys Pro
                245                 250                 255

Val Thr Glu Tyr Lys Glu Cys His Leu Ala Gln Val Pro Ser His Ala
            260                 265                 270

Val Val Ser Arg Ser Thr Asn Asp Lys Glu Glu Ala Ile Trp Glu Leu
        275                 280                 285

Leu Arg Gln Ser Gln Glu Lys Phe Gly Lys Lys Gln Ala Ser Gly Phe
    290                 295                 300

Gln Leu Phe Ala Ser Pro Ser Gly Gln Lys Asp Leu Leu Phe Lys Glu
305                 310                 315                 320

Ser Ala Ile Gly Phe Val Arg Val Pro Gln Lys Val Asp Val Gly Leu
                325                 330                 335

Tyr Leu Thr Phe Ser Tyr Thr Thr Ser Ile Gln Asn Leu Asn Lys Lys
            340                 345                 350

Gln Gln Asp Val Ile Ala Ser Lys Ala Arg Val Thr Trp Cys Ala Val
        355                 360                 365

Gly Ser Glu Glu Lys Arg Lys Cys Asp Gln Trp Asn Arg Ala Ser Arg
    370                 375                 380

Gly Arg Val Thr Cys Ile Ser Phe Pro Thr Thr Glu Asp Cys Ile Val
385                 390                 395                 400

Ala Ile Met Lys Gly Asp Ala Asp Ala Met Ser Leu Asp Gly Gly Tyr
              405                 410                 415

Ile Tyr Thr Ala Gly Lys Cys Gly Leu Val Pro Val Leu Ala Glu Asn
            420                 425                 430

Gln Lys Ser Ser Lys Ser Asn Gly Leu Asp Cys Val Asn Arg Pro Val
        435                 440                 445

Glu Gly Tyr Leu Ala Val Ala Val Arg Arg Glu Asp Ala Gly Phe
    450                 455                 460

Thr Trp Ser Ser Leu Arg Gly Lys Lys Ser Cys His Thr Ala Val Asp
465                 470                 475                 480

Arg Thr Ala Gly Trp Asn Ile Pro Met Gly Leu Leu Ala Asn Gln Thr
                485                 490                 495

Arg Ser Cys Lys Phe Asn Glu Phe Phe Ser Gln Ser Cys Ala Pro Gly
            500                 505                 510

Ala Asp Pro Lys Ser Asn Leu Cys Ala Leu Cys Ile Gly Asp Glu Lys
        515                 520                 525

Gly Glu Asn Lys Cys Ala Pro Asn Ser Lys Glu Arg Tyr Gln Gly Tyr
    530                 535                 540

Thr Gly Ala Leu Arg Cys Leu Ala Glu Lys Ala Gly Asn Val Ala Phe
545                 550                 555                 560

Leu Lys Asp Ser Thr Val Leu Gln Asn Thr Asp Gly Lys Asn Thr Glu
                565                 570                 575

Glu Trp Ala Arg Asn Leu Lys Leu Lys Asp Phe Glu Leu Leu Cys Leu
            580                 585                 590

Asp Asp Thr Arg Lys Pro Val Thr Glu Ala Lys Asn Cys His Leu Ala
        595                 600                 605

Ile Ala Pro Asn His Ala Val Val Ser Arg Thr Asp Lys Val Glu Val
    610                 615                 620

Leu Gln Gln Val Leu Leu Asp Gln Gln Val Gln Phe Gly Arg Asn Gly
625                 630                 635                 640

Gln Arg Cys Pro Gly Glu Phe Cys Leu Phe Gln Ser Lys Thr Lys Asn
                645                 650                 655

Leu Leu Phe Asn Asp Asn Thr Glu Cys Leu Ala Lys Ile Pro Gly Lys
            660                 665                 670

Thr Thr Ser Glu Lys Tyr Leu Gly Lys Glu Tyr Val Ile Ala Thr Glu
        675                 680                 685

Arg Leu Lys Gln Cys Ser Ser Ser Pro Leu Leu Glu Ala Cys Ala Phe
    690                 695                 700

Leu Thr Gln
705

<210> SEQ ID NO 4
<211> LENGTH: 688
<212> TYPE: PRT
<213> ORGANISM: Mus musculus

<400> SEQUENCE: 4

Lys Ala Thr Thr Val Gln Trp Cys Ala Val Ser Asn Ser Glu Glu Glu
1               5                   10                  15

Lys Cys Leu Arg Trp Gln Asn Glu Met Arg Lys Val Gly Gly Pro Pro
            20                  25                  30

Leu Ser Cys Val Lys Lys Ser Ser Thr Arg Gln Cys Ile Gln Ala Ile
        35                  40                  45

Val Thr Asn Arg Ala Asp Ala Met Thr Leu Asp Gly Gly Thr Met Phe
    50                  55                  60

```
Asp Ala Gly Lys Pro Pro Tyr Lys Leu Arg Pro Val Ala Glu Val
 65                  70                  75                  80

Tyr Gly Thr Lys Glu Gln Pro Arg Thr His Tyr Tyr Ala Val Ala Val
                 85                  90                  95

Val Lys Asn Ser Ser Asn Phe His Leu Asn Gln Leu Gln Gly Leu Arg
            100                 105                 110

Ser Cys His Thr Gly Ile Gly Arg Ser Ala Gly Trp Lys Ile Pro Ile
        115                 120                 125

Gly Thr Leu Arg Pro Tyr Leu Asn Trp Asn Gly Pro Pro Ala Ser Leu
    130                 135                 140

Glu Glu Ala Val Ser Lys Phe Ser Lys Ser Cys Val Pro Gly Ala
145                 150                 155                 160

Gln Lys Asp Arg Phe Pro Asn Leu Cys Ser Ser Cys Ala Gly Thr Gly
                165                 170                 175

Ala Asn Lys Cys Ala Ser Ser Pro Glu Glu Pro Tyr Ser Gly Tyr Ala
            180                 185                 190

Gly Ala Leu Arg Cys Leu Arg Asp Asn Ala Gly Asp Val Ala Phe Thr
        195                 200                 205

Arg Gly Ser Thr Val Phe Glu Glu Leu Pro Asn Lys Ala Glu Arg Asp
    210                 215                 220

Gln Tyr Lys Leu Leu Cys Pro Asp Asn Thr Trp Lys Pro Val Thr Glu
225                 230                 235                 240

Tyr Lys Glu Cys His Leu Ala Gln Val Pro Ser His Ala Val Val Ser
                245                 250                 255

Arg Ser Thr Asn Asp Lys Glu Glu Ala Ile Trp Glu Leu Leu Arg Gln
            260                 265                 270

Ser Gln Glu Lys Phe Gly Lys Lys Gln Ala Ser Gly Phe Gln Leu Phe
        275                 280                 285

Ala Ser Pro Ser Gly Gln Lys Asp Leu Leu Phe Lys Glu Ser Ala Ile
    290                 295                 300

Gly Phe Val Arg Val Pro Gln Lys Val Asp Val Gly Leu Tyr Leu Thr
305                 310                 315                 320

Phe Ser Tyr Thr Thr Ser Ile Gln Asn Leu Asn Lys Lys Gln Gln Asp
                325                 330                 335

Val Ile Ala Ser Lys Ala Arg Val Thr Trp Cys Ala Val Gly Ser Glu
            340                 345                 350

Glu Lys Arg Lys Cys Asp Gln Trp Asn Arg Ala Ser Arg Gly Arg Val
        355                 360                 365

Thr Cys Ile Ser Phe Pro Thr Thr Glu Asp Cys Ile Val Ala Ile Met
    370                 375                 380

Lys Gly Asp Ala Asp Ala Met Ser Leu Asp Gly Gly Tyr Ile Tyr Thr
385                 390                 395                 400

Ala Gly Lys Cys Gly Leu Val Pro Val Leu Ala Glu Asn Gln Lys Ser
                405                 410                 415

Ser Lys Ser Asn Gly Leu Asp Cys Val Asn Arg Pro Val Glu Gly Tyr
            420                 425                 430

Leu Ala Val Ala Ala Val Arg Arg Glu Asp Ala Gly Phe Thr Trp Ser
        435                 440                 445

Ser Leu Arg Gly Lys Lys Ser Cys His Thr Ala Val Asp Arg Thr Ala
    450                 455                 460

Gly Trp Asn Ile Pro Met Gly Leu Leu Ala Asn Gln Thr Arg Ser Cys
465                 470                 475                 480
```

-continued

```
Lys Phe Asn Glu Phe Phe Ser Gln Ser Cys Ala Pro Gly Ala Asp Pro
                485                 490                 495

Lys Ser Asn Leu Cys Ala Leu Cys Ile Gly Asp Glu Lys Gly Glu Asn
            500                 505                 510

Lys Cys Ala Pro Asn Ser Lys Glu Arg Tyr Gln Gly Tyr Thr Gly Ala
            515                 520                 525

Leu Arg Cys Leu Ala Glu Lys Ala Gly Asn Val Ala Phe Leu Lys Asp
    530                 535                 540

Ser Thr Val Leu Gln Asn Thr Asp Gly Lys Asn Thr Glu Glu Trp Ala
545                 550                 555                 560

Arg Asn Leu Lys Leu Lys Asp Phe Glu Leu Leu Cys Leu Asp Asp Thr
                565                 570                 575

Arg Lys Pro Val Thr Glu Ala Lys Asn Cys His Leu Ala Ile Ala Pro
            580                 585                 590

Asn His Ala Val Val Ser Arg Thr Asp Lys Val Glu Val Leu Gln Gln
            595                 600                 605

Val Leu Leu Asp Gln Gln Val Gln Phe Gly Arg Asn Gly Gln Arg Cys
    610                 615                 620

Pro Gly Glu Phe Cys Leu Phe Gln Ser Lys Thr Lys Asn Leu Leu Phe
625                 630                 635                 640

Asn Asp Asn Thr Glu Cys Leu Ala Lys Ile Pro Gly Lys Thr Thr Ser
            645                 650                 655

Glu Lys Tyr Leu Gly Lys Glu Tyr Val Ile Ala Thr Glu Arg Leu Lys
            660                 665                 670

Gln Cys Ser Ser Ser Pro Leu Leu Glu Ala Cys Ala Phe Leu Thr Gln
            675                 680                 685
```

COMPOSITION AND METHOD TO ENHANCE EXPRESSION OF HUMAN DEFENSIN 2

CROSS REFERENCE TO RELATED APPLICATIONS

This application claims priority to U.S. application Ser. No. 14/115,181, filed Nov. 1, 2013 (now abandoned), which is a US National Stage application of PCT/US12/36936, filed May 5, 2012, which claims the benefit of U.S. Provisional Patent Application Nos. 61/484,044 and 61/609,657 filed on May 9, 2011 and Mar. 12, 2012, respectively, the disclosures of which are hereby expressly incorporated by reference in their entirety.

STATEMENT REGARDING FEDERALLY SPONSORED RESEARCH

This invention was made with government support under HD061918 awarded by the National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 28 kilobytes ascii (text) file named "270915_ST25.txt," created on Oct. 31, 2017.

BACKGROUND

Inflammatory bowel disease (IBD) is a collective term used to describe related inflammatory disorders of the gastrointestinal tract whose etiology is not completely understood. The two most common forms of IBD are ulcerative colitis (UC) and Crohn's disease (CD). For most patients, IBD is a chronic condition with symptoms lasting for months to years. The course of IBD varies widely, with intermittent periods of remission (i.e., inactive disease) followed by periods of acute illness (i.e., active disease). Onset of IBD is predominant in young adulthood but can occur at any age.

IBD has no cure. Current therapies for IBD are directed at reducing the inflammatory process and at reducing the detrimental effects of the inflammatory process associated with the disease, and include administration of anti-inflammatory drugs (e.g., mesalamine, sulfasalazine, infliximab, adalimumab, prednisone, budesonide) and of immunosuppressive drugs (e.g., 6-mercaptopurine, azathioprine, cyclosporine). Such therapies are often associated with adverse side effects.

Hyaluronan, also referred to as hyaluronic acid or hyaluronate, is a non-sulphated glycosaminoglycan comprised of repeating disaccharide units of N-acetyl-glucosamine and B-glucuronic acid. Hyaluronan is distributed widely throughout connective tissue of all organs, and is important for maintaining tissue hydration, cushioning joints, preserving cell free space within specific tissues or regulation of cell behavior such as migration or proliferation via activation of cell signaling pathways. Hyaluronan is, under normal circumstances, a high molecular weight (HMW) glycosaminoglycan, which is produced mainly by fibroblasts. As disclosed herein compositions comprising hyaluronan of specific sizes (about 10 to about 35 kDa) is used to treat intestinal conditions and improve intestinal health in patients.

SUMMARY

Applicants have found that oral administration of specific sized hyaluronan fragments (approximately 35 kDa) reduces the severity of bacterially-driven colitis in mouse models. Accordingly, as disclosed herein compositions comprising low molecular weight hyaluronan are provided for oral administration to improve intestinal health in individuals. More particular, hyaluronan fragments of 10-75 kDa, and more typically about 35 kDa, have been discovered to induce anti-microbial protein production by epithelial cells that line the intestine. Additionally, applicants have found that hyaluronan fragments of molecular weight less than 10 kDa, more particularly at about 4.7 kDA, inhibits the anti-microbial protein production of epithelial cells induced by 35 kDa hyaluronan. One of the anti-microbial protein proteins induced by 35 kDa hyaluronan is human beta defensin 2, which is known to play an important role in protecting against intracellular and extracellular pathogens. Human β-defensin 2 is a small protein (7 kDa) with broad spectrum microbicidal activity. The protein is not constitutively expressed, but is regulated by TLR signaling. Accordingly, in one embodiment compositions comprising hyaluronan fragments of 10-75 kDa, and exclude hyaluronan fragments less than 10 kDa, are used to treat patients suffering from intestinal inflammation and/or intestinal bacterial infection.

In one embodiment, hyaluronan fragments of about 35 kDa are combined with known probiotics components and orally administered (either alone or in combination with other active agents) to individuals susceptible to intestinal infections or other intestinal distress. In one embodiment the low molecular weight hyaluronan is combined with lactoferrin. Lactoferrin is a multifunctional globular protein of the transferrin family with a molecular mass of about 80 kDa that is widely represented in various secretory fluids, such as milk, saliva, tears, and nasal secretions. In one embodiment a composition comprising hyaluronan fragments of 10-75 kDa, and more typically about 35 kDa, and lactoferrin is provided. More particularly, the composition is formulated for oral delivery using an oral pharmaceutically acceptable carrier. Such a composition provides enhanced protection to epithelial surfaces, especially those in contact with the external environment, including for example the intestine, skin and lung cells, wherein the protective effect is greater than that achieved by either component by itself.

In one embodiment the hyaluronan comprising compositions, formulated for oral delivery, are used to treat patients suffering from a medical condition (e.g., Crohn's disease) or a medical treatment (e.g., antibiotics or radiation treatments) that disrupts normal intestinal flora and intestinal function. The composition can be administered prophylactically, or can be administered after the onset of the symptoms.

BRIEF DESCRIPTION OF THE DRAWINGS

FIG. 6B is a reverse transcriptase PCR analysis of RNA isolated from human colon epithelium cells (HT29 cells) treated with various hyaluronan containing compositions, demonstrating the enhanced transcription induced by HA35 and milk protein fragments. Lane 1 is a base pair size standard, lane 2 is a control (no protein), lane 3 is HA 4.7 kDa fragments, lane 4 is HA 35 kDa fragments, lane 5 is human milk fragments and lane 6 is human milk fragments pretreated with hyaluronidase prior to contact with the cells. Only the HA 35 kDa fragments and the human milk fragments produced a substantial increase in HBD2 RNAs, whereby beta actin served as a loading control. Pretreating the human milk fragments with hyaluronidase eliminated that compositions ability to stimulate HBD2 RNA production.

DETAILED DESCRIPTION

Definitions

Figure 1:
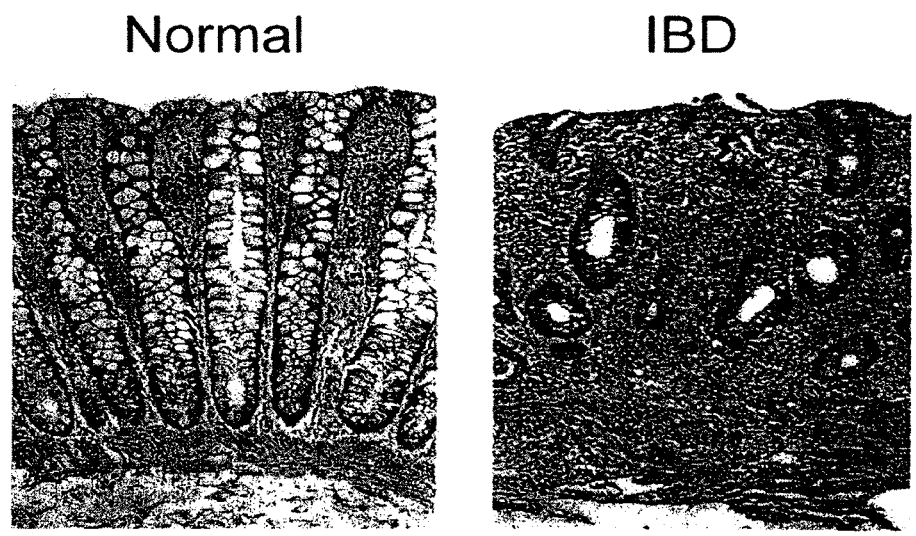
FIG. 1. provides a comparison of a crossection of human colonic mucosa, demonstrating the changes that occur during an Inflammatory Bowel Disease flare in humans, including edema, epithelial/crypt loss, expansion of smooth muscle layer and leukocyte infiltration.
Figure 2:
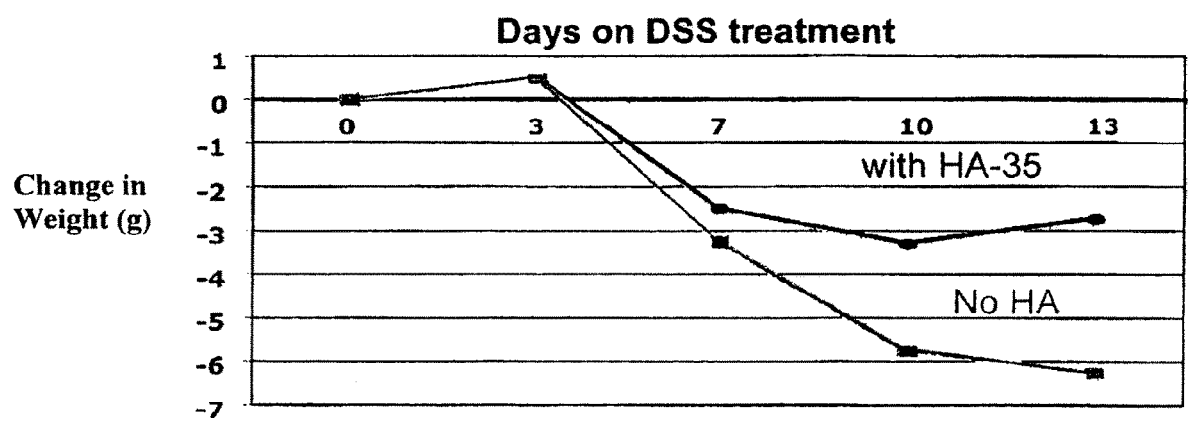
FIG. 2 shows the changes in weight of mice treated with 2.5% dextran sodium sulfate (DSS) in their drinking water in the presence or absence of 35 kDa hyaluronan. Treatment with 2.5% dextran sodium sulfate (DSS) reproducibly initiates colitis and such treated mice are used as a model of colitis. The data shows that co-administration of 35 kDA hyaluronan provides a protective effect from DSS induced colitis.
Figure 3:
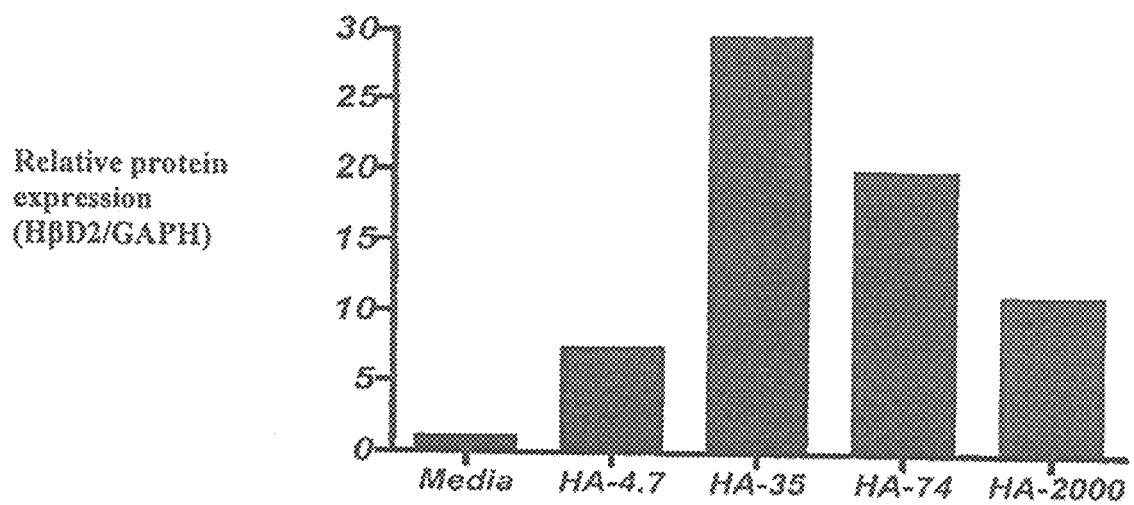
FIG. 3 is a graph showing the induction of Human β-defensin by hyaluronan in HT29 colon epithelial cells. Human β-defensin is induced by hyaluronan in a size dependent manner.
Figure 4A:
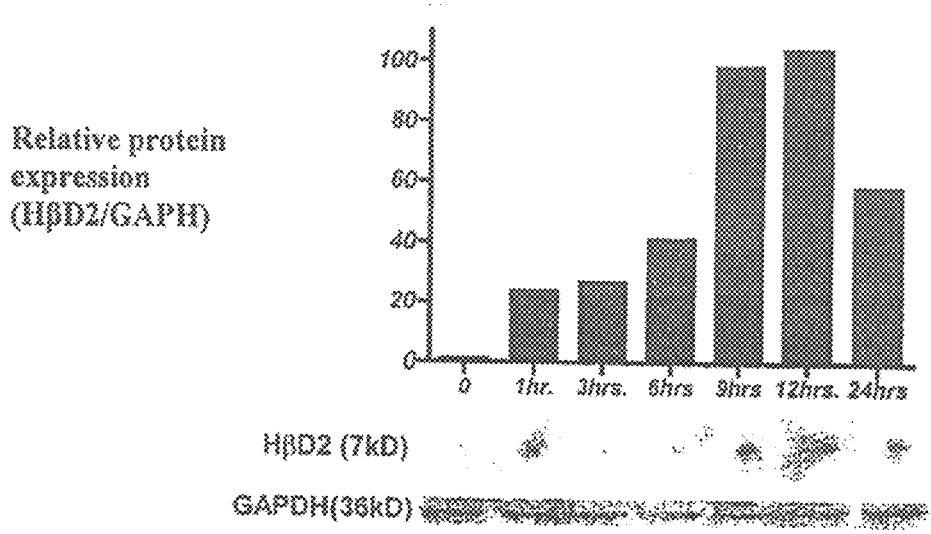
FIGS. 4A & 4B are graphs showing that the induction of Human β-defensin by hyaluronan in HT29 colon epithelial cells is both time (See FIG. 4A) and concentration (FIG. 4B) dependent.
Figure 4B:
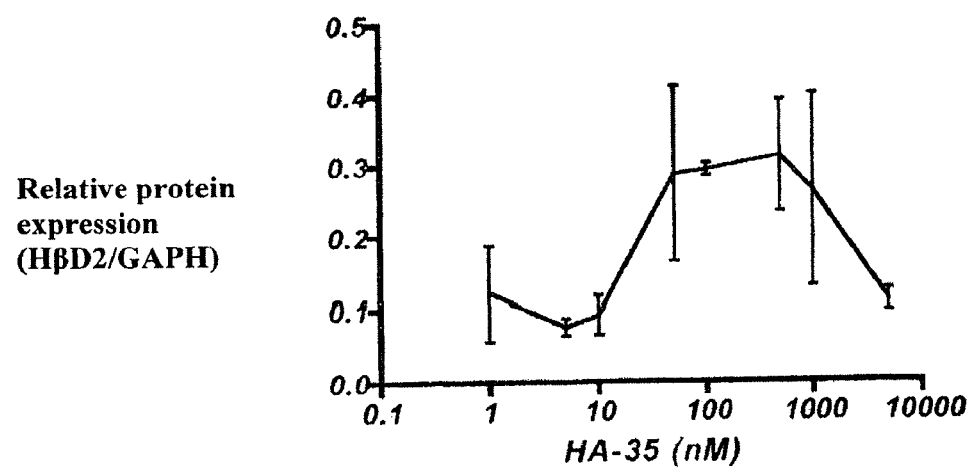
Figure 5:
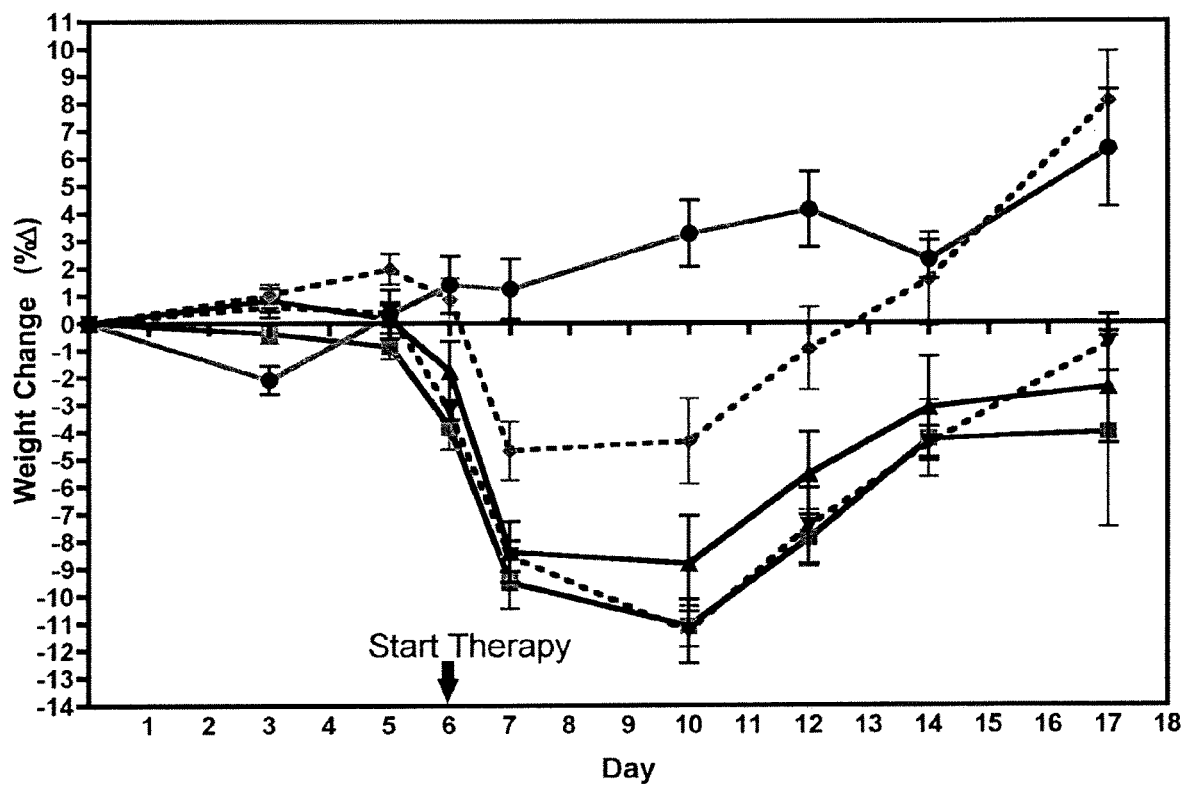
FIG. 5 is a graph presenting data showing the efficacy of 35 kDA hyaluronan and lactoferrin in treating DSS induced colitis. Mice were administered 2.5% dextran sodium sulfate (DSS) in their drinking water for three days. Starting on day 4 and proceeding through day 12, the mice were divided into four groups and received one of four treatments daily by gavage: 1) 35 kDA hyaluronan (-※-); 2) lactoferrin (-▼-) a combination of 35 kDA hyaluronan and lactoferrin (-✻-); or 4) water (-▲-), as the control. In addition a fifth group of mice were not administered 2.5% dextran sodium sulfate (DSS) and served as a healthy control (-●-). Only the HA 35-lactoferrin treatment group recovered weight to the non-colitis control levels.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable.

As used herein, the term "treating" includes alleviation of the symptoms associated with a specific disorder or condition and/or preventing or eliminating said symptoms.

As used herein the term "patient" without further designation is intended to encompass any warm blooded vertebrate domesticated animal (including for example, but not limited to livestock, horses, cats, dogs and other pets) and humans.

The term "co-administered" as used herein refers to the administration of two compounds or compositions as part of a single therapeutic regiment. The first and second compounds/composition may be administered together as a mixture as a single dosage form or as separate, multiple dosage forms. Alternatively, the first and second compounds/composition may be administered consecutively to one another as two separate and distinct dosage forms. However, when two or more therapeutic agents are co-administered, each of the separate therapeutic agents are administered within a timeframe wherein the first therapeutic agent is still active in vivo upon administration of the second therapeutic agent or treatment. The co-administration of two or more therapeutic agents to a patient does not preclude the separate administration of any of those same therapeutic agents or any other active compound to the patient at another time during a course of treatment.

As used herein the term "colitis" refers to an inflammation of the large intestine (colon, caecum and rectum).

Embodiments

Hyaluronan is a carbohydrate polymer that is normally deposited in connective tissues around cells of vertebrate animals. Applicants have discovered that oral administration of low molecular weight hyaluronan fragments ranging from about 10 to about 75 kDa, and more particularly ranging from about 15 to about 50 kDa induce antimicrobial protein production by epithelial cells that line the intestine. One such induced protein is human beta defensin 2, a protein important in protecting against intracellular pathogens.

Surprisingly, applicants have discovered that hyaluronan fragments of less than 10 kDa, and more particularly of about 4.7 kDa, inhibit the antimicrobial protein production of epithelial cells that is induced by contacting the cells with hyaluronan fragments ranging from about 10 to about 75 kDa. In accordance with one embodiment a composition of low molecular weight hyaluronan fragments ranging from about 10 to about 75 kDa, is provided wherein said composition is substantially free of haluaronan fragments having a molecular weight of less than 10 kDa. In accordance with one embodiment hyaluronan fragments of less than 10 kDa fail to be detected in the compositions based on polyacrylamide gel electrophoresis analysis or by absorbance detection methods. In one embodiment NaCl elution of specific fragment size ranges is used to alter the HA fragment MW distribution of HA35, removing inhibitory small fragments. In accordance with one embodiment elution of the hyaluronan fragments is conducted at 1.00 M NaCl or higher to eliminate HA4.7 from the recovered hyaluronan fragments. In accordance with one embodiment a composition comprising hyaluronan fragments ranging from about 10 to about 75 kDa is provided wherein haluaronan fragments having a molecular weight of less than 10 kDa comprise less than 1, 0.5, 0.1, 0.05, or 0.001% of the hyaluronan content of the composition. In accordance with one embodiment a composition comprising hyaluronan fragments is provided wherein the hyaluronan component of said composition consists essentially of hyaluronan fragments having an mean distribution of about 25 to about 45 kDa, and in a further embodiment the composition comprises less than 1, 0.5, 0.1, 0.05, or 0.001% of haluaronan fragments having a molecular weight of less than 10 kDa relative to the total detectable hyaluronan content. In one embodiment the hyaluronan compositions disclosed herein comprise less than 1% or less than 0.5% of haluaronan fragments having a molecular weight of 4.7 kDa or less relative to the total hyaluronan content of the composition.

In one embodiment a composition for increasing human beta defensin 2 production is provided wherein the composition comprises hyaluronan fragments having a molecular weight of about 35 kDa, and a pharmaceutically acceptable carrier suitable for oral administration, with the proviso that the composition is substantially free of hyaluronan fragments of less than 10 kDa. In one embodiment the composition comprises hyaluronan fragments within the range of about 15 kDa to about 75 kDa, 25 to about 50 kDa or about 30 to about 45 kDa. In one embodiment the composition is substantially free of hyaluronan fragments of about 4.7 kDa. In one embodiment a composition is provided comprising low molecular weight hyaluaronan and a pharmaceutically acceptable carrier, wherein the hyaluaronan component of the composition consists essentially of hyaluronan fragments within the range of about 25 to about 50 kDa, or having an average molecular weight of about 35 kDa.

Applicants have found that compositions comprising hyaluronan fragments having a molecular weight of about 35 kDa, but are substantially free of hyaluronan fragments of less than 10 kDa, have efficacy in protecting and treating intestinal disorders including for example Crohn's Disease (CD). As shown in Table 1 patients suffering from active Crohn's Disease experience a large drop in human beta defensin 2 (HBD2) that is recovered in some degree during remission.

TABLE 1

| Patient Group | N | Median Concentration of HD-5, ng/ml (IQR) | N | Median Concentration of HBD2, pg/ml (IQR) |
|---|---|---|---|---|
| Healthy individual | 33 | 12.0 (7.0, 21.9)* | 13 | 280 (170, 555)† |
| Active CD | 32 | 18.4 (11.6, 49.6)* | 12 | 20 (0, 360)† |
| CD in remission | 17 | 9.0 (6.2, 18.0) | 11 | 90 (40, 370) |

Accordingly, one embodiment of the present disclosure comprises administering a composition comprising hyaluronan fragments having a molecular weight of about 35 kDa, with the proviso that the composition is substantially free of hyaluronan fragments of less than 10 kDa, to a patient suffering an intestinal disease or condition. In one embodiment the administered composition comprises hyaluronan fragments within the range of about 15 kDa to about 75 kDa, 25 to about 50 kDa or about 30 to about 45 kDa. In a further embodiment the administered composition comprises less than 1, 0.5, 0.1, 0.05, or 0.001% of haluaronan fragments having a molecular weight of less than 10 kDa, relative to the total hyaluronan content. In one embodiment the administered hyaluronan composition comprises less than 1%, or less than 0.5%, of haluaronan fragments having a molecular weight of 4.7 kDa or less, relative to the total hyaluronan content of the composition. In one embodiment the composition is substantially free of hyaluronan fragments of about 4.7 kDa. In one embodiment the hyaluronan compositions disclosed herein are used to treat Crohn's Disease or colitis. In particular, applicants observed that the oral administration of low molecular weight hyaluronan reduces the severity of bacterially-driven colitis in mouse models.

Accordingly, in one embodiment the hyaluaronan compositions disclosed herein are used to treat any patient susceptible to intestinal bacterial infections or subject to intestinal inflammatory conditions caused by chronic disease. In accordance with one embodiment compositions are provided to enhance the intestinal health of the patient or treat any patient susceptible or suffering from compromised intestinal functioning. A patient with compromised intestinal functioning is intended to include any patient suffering from inflammation and/or bacterial infection, or other condition that negatively impacts the functioning of the intestines.

The compositions disclosed herein can be used to prophalactically treat a chronic condition, and thus prevent symptoms associated with a medical condition (e.g., Crohn's disease), or a medical treatment (e.g., antibiotics or radiation treatments), that disrupts normal intestinal flora and intestinal function. Alternatively, the composition can be administered after the onset of the symptoms or after exposure to agents that disrupt normal intestinal flora and intestinal function. In one embodiment the compositions disclosed herein are administered to patients suffering from colitis, including inflammatory bowel diseases such as ileitis, ulcerative colitis, Barrett's syndrome, and Crohn's disease.

In accordance with one embodiment a composition comprising low molecular weight hyaluronan is provided for enhancing the intestinal health of the patient, wherein the composition is substantially free of hyaluronan fragments of less than 10 kDa, and more particularly, substantially free of hyaluaronan fragments of about 4.7 kDa. As used herein, low molecular weight hyaluronan is intended to encompass hyaluronan fragments ranging in size anywhere between 10 kDa to 75 kDa, 10 kDa to 50 kDa, 20 kDa to 45 kDa and 30 kDa to 40 kDa. In one embodiment the hyaluronan is about 35 kDa in size. In one embodiment the compositions are substantially free of hyaluronan fragments having a molecular weight of less than 10 kDa or having a molecular weight of about 4.7 kDa of less. The hyaluronan compositions are formulated for oral delivery using a pharmaceutically acceptable carrier suitable for oral administration.

Formulations suitable for oral administration of the hyaluronan compositions disclosed herein can consist of (a) liquid solutions, such as an effective amount of hyaluronan dissolved in diluents, such as water, saline, or juice; (b) capsules, sachets, tablets, lozenges, and troches, each containing a predetermined amount of the active ingredient, as solids or granules; (c) powders; (d) suspensions in an appropriate aqueous liquid or non-aqueous liquid; packed in liposome's; or as a bolus, etc.; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, manifold, corn starch, potato starch, agonic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise hyaluronan in a flavor, usually sucrose and acacia or tragacanth, as well as pastilles comprising hyaluronan in an inert base, such as gelatin and glycerin, or sucrose and acacia, emulsions, gels, and the like containing, in addition to, such excipients as are known in the art.

Hyaluronan fragments having a size of about 10 kDa to about 75 kDa have also been found to stimulate interferon-mediated pathways. Accordingly, in one embodiment compositions comprising 10 kDa to about 75 kDa hyaluronan, but optionally substantially free of hyaluronans having a molecular weight of less than 10 kDa, are administered to patients as a defense against pathogens, including intestinal pathogens. In one embodiment the compositions are administered prophalactically, and in another embodiment the compositions are administered after known or suspected contact with an intestinal pathogen as a means of minimizing or preventing compromised intestinal function. In accordance with one embodiment a method of stimulating interferon-mediated pathways is provided wherein a patient is orally administering a pharmaceutical composition comprising a purified hyaluronan, wherein the hyaluronan has a molecular weight within the range of about 5 to about 50 kDa. Optionally the composition is substantially free of hyaluronan fragments of 4.7 kDa or less. In one embodiment the composition comprises hyaluronan fragments averaging about 35 kDa in size. In one embodiment a composition comprising hyaluronan having a molecular weight of about 5 to about 25 kDa is administered to patients as a defense against rotavirus infection.

Composition comprising hyaluronan having a molecular weight of about 5 kDa have been found to induce defensin expression in monkey cells. In accordance with one embodiment compositions and methods are provided to induce anti-microbial protein production by epithelial cells that line the intestine and thus improve intestinal health in individuals. The method comprises administering orally to mammalian species a composition comprising relatively small molecular weight hyaluronan. More particularly, hyaluronan fragments of 10-50 kDa, and more typically about 35 KDa, have been discovered to enhance production of human beta defensin 2, which is known to play an important role in protecting against intracellular pathogens. In one embodiment, oral administration of hyaluronan fragments of about 10 to about 50 KDa is formulated as a probiotic (either alone or in combination with other active agents) to individuals susceptible to intestinal infections or other intestinal distress. In another embodiment the oral composition is formulated for treating patients suffering from a medical condition (e.g., Crohn's disease) or a medical treatment (e.g., antibiotics or radiation treatments) that disrupts normal intestinal flora and intestinal function.

In accordance with one embodiment a composition is provided comprising low molecular weight hyaluronan and a probiotic. More particularly, in one embodiment about 10 to about 50 kDa or about 10 to about 35 kDa sized hyaluronan is co-administered orally with a standard probiotic as a therapy to 1) aid infants susceptible to intestinal infection or infants not being breast fed; 2) aid patients whose medical condition (e.g., Crohn's disease) or medical treatment (e.g., antibiotics and radiation therapy) removes much of the beneficial intestinal flora that normally protects the intestine. In one embodiment compositions comprising about 10 to about 35 kDa sized hyaluronan are used as an adjunct to currently available bacterial probiotic treatments. Hyaluronan fragments of about 10 to about 50 kDa or about 10 to about 35 kDa in size can be co-administered either as a separate composition relative to the bacterial probiotic formulation or alternatively can be mixed with current bacterial probiotic formulations and administered as a single composition.

Suitable probiotics include a plurality of beneficial microorganisms (such as lactobacilli, acidophilus, and other yogurt cultures), enzymes, or combinations thereof. Suitable probiotics also include any substance that promotes the growth of beneficial microorganisms in the composition or subject to which the composition is administered, either alone or in combination with other probiotics.

The low molecular weight hyaluronan compositions disclosed herein can be further combined with other known agents that enhance intestinal health, including for example glucosamine. The compositions can also comprise at lease one electrolyte, vitamin, mineral or trace element. Suitable electrolytes include sodium, potassium and calcium, and can be present in the composition in a concentration of between about 0.1% and about 50%, including any fractional percentage in intervals of about 0.01%. Suitable vitamins and minerals include typical adult daily dosages, for example: Vitamin A (about 1000 to about 10,000 IU; Vitamin B1 or thiamine (about 50 mg); Vitamin B2 or riboflavin (about 50 mg); Vitamin B3 as niacin or niacinamide (about 50 to about 500 mg); Vitamin B5 or pantothenic acid (about 50 to about 100 mg); Vitamin B6 or pyridoxine (about 50 m); Vitamin B12 (about 300 to about 1000 mcg); Biotin (about 300 mcg); Choline (about 100 mg); Folic acid (about 800 mcg); Inositol (about 100 mg); Para-aminobenzoic acid (about 50 mg); Vitamin C (about 50 mg to about 3000 mg or more, in multiple daily doses); Bioflavonoids (mixed—about 500 mg); Hesperidin (about 100 mg); Rutin (about 25 mg); Vitamin D (about 400 IU); Vitamin E (about 200 to about 600 IU); Vitamin K (about 100 mcg); Apatite (for example micocrystalline hydroxyapaptite—about 4762 mcg; Chromium (about 150 mcg); Copper (about 3 mg); Iodine (about 225 mcg); Iron (about 18 mg); Magnesium (about 750 to about 1,000 mg); Manganese (about 10 mg); Molybdenum (about 30 mcg); and Selenium (about 200 mg); and Zinc (about 50 mg) can also be included in the compositions of the present disclosure. Greater or lesser amounts of vitamins, minerals or trace elements for use in the composition are also contemplated.

Applicants have discovered that human milk contains hyaluronan. Importantly, the size of the hyaluronan purified from milk includes hyaluronan fragments of the same size as the active, purified fragments that induce anti-microbial activity. Furthermore, the levels of hyaluronan in the mother's milk are highest immediately after delivery and decrease over approximately 10 weeks to a steady lower level. The infant formula products derived from cow's milk do not have levels of hyaluronan as high as in human milk during early lactation, and soy based infant formula has none. Accordingly, one aspect of the present invention is to supplement current standard infant formula with hyaluronan, having a molecular weight of about 10 to about 50 kDa or about 10 to about 35 kDa, to match the hyaluronan concentrations typically found in human milk during the first few months of lactation. Such hyaluronan supplemented infant formulas can be further supplemented with the addition of an external source of lactoferrin.

Lactoferrin (a protein) is one component contained in milk, that forms complexes with hyaluronan and is secreted by many types of epithelial lining cells. Other investigators have shown that lactoferrin has direct anti-microbial properties and inhibits certain inflammatory responses at epithelial surfaces in the intestine and on the skin. Lactoferrin is a multifunctional globular protein of the transferrin family with a molecular mass of about 80 kDa that is widely represented in various secretory fluids, such as milk, saliva, tears, and nasal secretions. Lactoferrin is one of the components of the immune system of the body, has antimicrobial activity (bacteriocide, fungicide) and is part of the innate defense, mainly at mucoses. In particular, lactoferrin provides antibacterial activity to human infants.

Accordingly, in one embodiment the low molecular weight hyaluronan compositions disclosed herein may be further combined with, or co-administered with, lactoferrin to provide an enhanced protection to epithelial surfaces wherein the protective effect is greater than that achieved by either component by itself, especially for epithelial surfaces in contact with the external environment, for example the intestine, skin and lung. This unique combination is particularly beneficial to infants and individuals susceptible to intestinal infections or other intestinal distress including premature infants or infants that are formula fed; patients with intestinal inflammatory conditions caused by chronic disease; patients who are immunocompromised; patients undergoing chemotherapy; or radiation therapy for cancer; patients susceptible to nosocomial intestinal infection due to prolonged hospital or nursing home stays; patients suffering from a medical condition (e.g., Crohn's disease) or a medical treatment (e.g., antibiotics or radiation treatments) that disrupts normal intestinal flora and intestinal function. Such compositions are anticipated to have enhanced protective effects on epithelial surfaces especially those in contact with the external environment, including for example the intestine, skin and lung cells.

In accordance with one embodiment a pharmaceutical composition for inhalation is provided for enhancing the health of lung tissues and prevent or remove/diminish bacterial infections of the lung. Any standard device can be used to administer the hyaluronan compositions, including the hyaluronan/lactoferrin compositions, to the lung to treat pulmonary infections. In accordance with one embodiment the hyaluronan compositions disclosed herein are administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031.

In accordance with one embodiment a pharmaceutical composition for oral administration is provided for enhancing intestinal health. In one embodiment the composition comprises hyaluronan having a molecular weight within the range of about 15 to about 50 KDa, lactoferrin, and a pharmaceutically acceptable carrier suitable for oral administration. Optionally the compositions are substantially free of hyaluronan fragments having a molecular weight of 10 kDa or less, and in one embodiment are substantially free of hyaluronan fragments having a molecular weight of 4.7 kDa or less. In one embodiment the combination of low molecular weight hyaluronan and lactoferrin is also used as an adjunct to current probiotic (beneficial bacteria) treatments or as an adjunct to current infant formula compositions. In accordance with one embodiment a composition is provided comprising hyaluronan having a molecular weight within the range of about 5 to about 75 kDa, 10 to about 50 kDa, 25 to about 35 kDa or about 35 kDa, lactoferrin, and a pharmaceutically acceptable carrier suitable for oral administration. In one embodiment the lactoferrin is selected from mammalian species, including for example bovine, mouse or human lactoferrin proteins. In one embodiment the lactoferrin is human lactoferrin. In one embodiment the lactoferrin protein comprises the sequence of SEQ ID NO: 1, SEQ ID NO: 2, SEQ ID NO: 3, SEQ ID NO: 4 or a fragment or derivative of any of those sequences. In a further embodiment the lactoferrin protein comprises an amino acid sequence that shares 70%, 80%, 85%, 90%, 95% or 99% sequence identity with SEQ ID NO: 1, SEQ ID NO: 2, SEQ ID NO: 3, SEQ ID NO: 4. In one embodiment the lactoferrin protein comprises the sequence of SEQ ID NO: 2.

In accordance with one embodiment, in compositions comprising lactoferrin and hyaluronan, the lactoferrin and hyaluronan are conjugated to one another. Conjugates are formed by linking lactoferrin and hyaluronan, either directly, or indirectly through a linker. Such linkages can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other. In one embodiment the lactoferrin protein can be linked to hyaluronan via direct covalent linkage by reacting targeted amino acid residues of the peptide with an organic derivatizing agent that is capable of reacting with reactive groups present on hyaluronan.

In one embodiment the hyaluronan and lactoferrin are covalently linked to one another via a bifunctional linker. In another embodiment the hyaluronan and lactoferrin are linked to a common lipid vesicle, such as a liposome or a micelle. More particularly, in one embodiment the hyaluronan and lactoferrin are linked by covalent coupling to the exterior surface of the liposome or alternatively, one or both compounds can be linked by entrapping the compound within the liposome interior space.

In accordance with one embodiment a method of treating patients in need of improved intestinal function is provided. The method comprises the steps of identifying patients suffering from compromised intestinal function, and orally administering a low weight hyaluronan composition as disclosed herein, where said hyaluronan has a molecular weight within the range of about 5 to about 75 kDa, about 25 to about 50 kDa or about 35 kDa. Optionally the composition is substantially free of hyaluronan having a molecular weight of about 4.7 kDa or less. In one embodiment the patients in need of improved intestinal function include infants and individuals susceptible to intestinal infections or other intestinal distress including premature infants or infants that are formula fed; patients with intestinal inflammatory conditions caused by chronic disease; patients who are immunocompromised; patients undergoing chemotherapy or radiation therapy for cancer; patients susceptible to nosocomial intestinal infection due to prolonged hospital or nursing home stays, patients suffering from a medical condition (e.g., Crohn's disease) or a medical treatment (e.g., antibiotics or radiation treatments) that disrupts normal intestinal flora and intestinal function. In one embodiment the low molecular weight hyaluronan composition further comprises lactoferrin.

In accordance with one embodiment a method of treating active colitis is provided. The method comprises the steps of identifying patients suffering from compromised intestinal function, and orally administering a low weight hyaluronan composition as disclosed herein, where said hyaluronan has a molecular weight within the range of about 10 to about 75 kDa, about 25 to about 50 kDa or about 35 kDa. In one embodiment the low molecular weight hyaluronan composition further comprises lactoferrin. In one embodiment the patient is suffering from an inflammatory bowel disease, including for example Crohn's disease.

In one embodiment a kit is provided for administering the low molecular weight hyaluronan compositions to a patient. In one embodiment the kit comprises the low molecular weight hyaluronan composition and a device for administering the composition to a patient. Depending on the route of administration, the kit may include an inhaler if said composition is an inhalable composition; a spoon, pump, or a vessel with or without volume markings if said composition is an oral liquid composition; or any other measuring or delivery device appropriate to the dosage formulation of the composition present in the kit.

The kit may alternatively, or in addition, include one or more containers, e.g., vials, tubes, bottles, optionally containing the low molecular weight hyaluronan composition in a lyophilized form or in an aqueous solution. Preferably, the kits will also include instructions for use. In one embodiment, the kits of this invention may comprise in a separate container a pharmaceutical composition comprising a second therapeutic agent, for co-administration with hyaluronan. In one embodiment the second therapeutic composition comprises lactoferrin.

Example 1

Combination of HA-35 and lactoferrin promotes recovery from DSS-induced colitis in mice.

Colitis Model: Age matched male C57Bl/6 mice were treated with 2.5% dextran sodium sulfate (DSS) in their drinking water for five days, a treatment which reproducibly initiates colitis. DSS treatment was discontinued and normal drinking water was supplied immediately after the first treatment (see below).

Treatment: Subsequently, groups of mice were given one of four treatments delivered once per day by oral gavage (single dose delivered into the stomach) for up to 12 days. The four treatments were:
1) water (250 µl);
2) 300 µg HA-35 (in 250 µl water);
3) 600 mg lactoferrin (in 250 µl water);
4) 300 µg hyaluronan and 600 µg lactoferrin (in 250 µl water). Treatment 4 is a 1:1 molar ratio of hyaluronan 35 to lactoferrin.

Animals were weighed at regular intervals throughout the treatment, and harvested in groups of 5 at days 1, 4, 8 and 11 after beginning treatment, for histological examination of the colon tissue. The results obtained from groups of mice receiving treatments were compared with the results of a group of age and sex matched control animals that did not receive DSS and therefore did not get colitis. Additionally a group of animals that had colitis induced, but never received any treatment was harvested on Day 5, and used as a positive control.

Results: Mice undergoing intestinal inflammation lose weight, a reflection of organ dysfunction. Consistent with this colitis model, groups of mice that were treated with DSS lost weight for five days after discontinuing treatment. Mice treated with water, HA-35, or lactoferrin alone partially recovered, all three treatment groups rising to the same level, over the next week. However the group receiving HA-35 plus lactoferrin recovered weight more rapidly and completely returned to the non-DSS control levels one week later. The average level of histological damage of each group at each time point overall paralleled the weight loss and subsequent gain. Again, the hyaluronan plus lactoferrin group was most like the untreated control at the end of the experiment. These results indicate a synergistic effect of the combined HA-35/lactoferrin treatment and not merely an additive effect of the two active components.

Example 2

In Vitro Cell Response of Endothelial Cells to Hyaluronan

Cell Culture—HT29 epithelial cells, a line initially derived from a human intestinal tumor, were washed and plated at a 1:15 area:area ratio in 12-well plates (Becton Dickinson, Franklin Lakes, N.J.) and cultured in RPMI medium supplemented with 10% fetal bovine serum (FBS) and incubated at 37° C. in a humidified environment containing 5% $CO_2$ until 70-80% confluent (3 days). Purified, lyophilized HA was purchased from Lifecore Biomedical, LLC, Chaska, Minn. The HA size designations were made on the basis of average molecular weight: 4.7 kDa (HA-4.7), 35 kDa (HA-35), 2000 kDa (HA-2M). The final concentrations of HA fragment-supplemented medium treatments are as follows: HA4.7 alone at 0.047 m/ml (10 µM), HA35 alone at 0.35 mg/ml (10 µM), HA2M alone at 0.35 mg/ml (0.18 µM), HA4.7 with HA35 at 0.047 mg/ml and 0.35 mg/ml respectively, and HA35 with HA2M at 0.35 mg/ml and 0.35 mg/ml respectively. Fragment-supplemented medium treatments containing HA35 and either HA4.7 or HA2M were prepared by adding the HA4.7 or HA2M to an original purified HA35 preparation.

On the day of the experiment, growth medium was removed, and the HT29 cells were treated with fresh RPMI containing 10% FBS without or with specific or mixed molecular weight range HA preparations listed above for a total of 8 hours before the harvest of whole cell lysates and subsequent Western blot analysis. A total of 12 replicate cell culture wells per group were treated in this manner.

Detection of HβD2 by Immunoblot (Western) Analysis—Whole cell lysates from HT29 cells were isolated for Western blotting in the following lysis buffer: 300 mM NaCl, 50 mM Tris pH 8.0, 0.5% NP-40, 1 mM EDTA, 10% glycerol, protease inhibitor for mammalian tissue P8340 (Sigma-Aldrich Inc., St. Louis, Mo.). Cell lysate proteins were separated by SDS-PAGE using pre-cast Tricine based 4-20% gradient gels (Invitrogen, Carlsbad, Calif.). Separated proteins were transferred at 4° C. to PVDF membrane by electroblotting apparatus (Bio-Rad Laboratories, Hercules, Calif.) at 100 V for 45 m. PVDF membranes were air-dried at room temperature for 60 m prior to blocking with Odyssey Blocking Buffer (LI-COR Biosciences, Lincoln, Nebr.) diluted to 50% concentration in Tris-buffered saline. The membrane was incubated with rabbit polyclonal antibody against HβD2 at 1:50 (Abcam, Cambridge, Mass.), and the primary antibody was followed by biotin conjugated anti-rabbit IgG at 1:25,000 (Jackson ImmunoResearch Laboratories Inc., West Grove, Pa.), and finally horseradish peroxidase (HRP)-conjugated streptavidin was added at 1:100,000 (GE Healthcare, Piscataway, N.J.). Membrane-bound GAPDH protein expression was detected by incubation with rabbit polyclonal antibody against GAPDH at 1:5,000 (Abcam, Cambridge, Mass.) followed by HRP-conjugated donkey polyclonal anti-rabbit IgG (1:20,000, GE Healthcare, Piscataway, N.J.). All washing steps were conducted in Tris-buffered saline with 0.1% Tween-20. Protein bands were visualized using ECL plus chemiluminescent development (GE Healthcare, Piscataway, N.J.) and detection by BioMax XAR scientific imaging film (Carestream Health Inc., Rochester, N.Y.). Differences in chemiluminescent signal intensity were quantified using the NCBI ImageJ software package.

Statistical analysis—Statistical difference between treatment groups was evaluated where appropriate by unpaired one-tailed Student's t-test and all error bars drawn to indicate the standard error of the means (S.E.M.). Differences were considered significant when $P<0.05$. Statistical analysis and graphing was completed using GraphPad Prism version 4.0 c.

Results

Figure 6A:
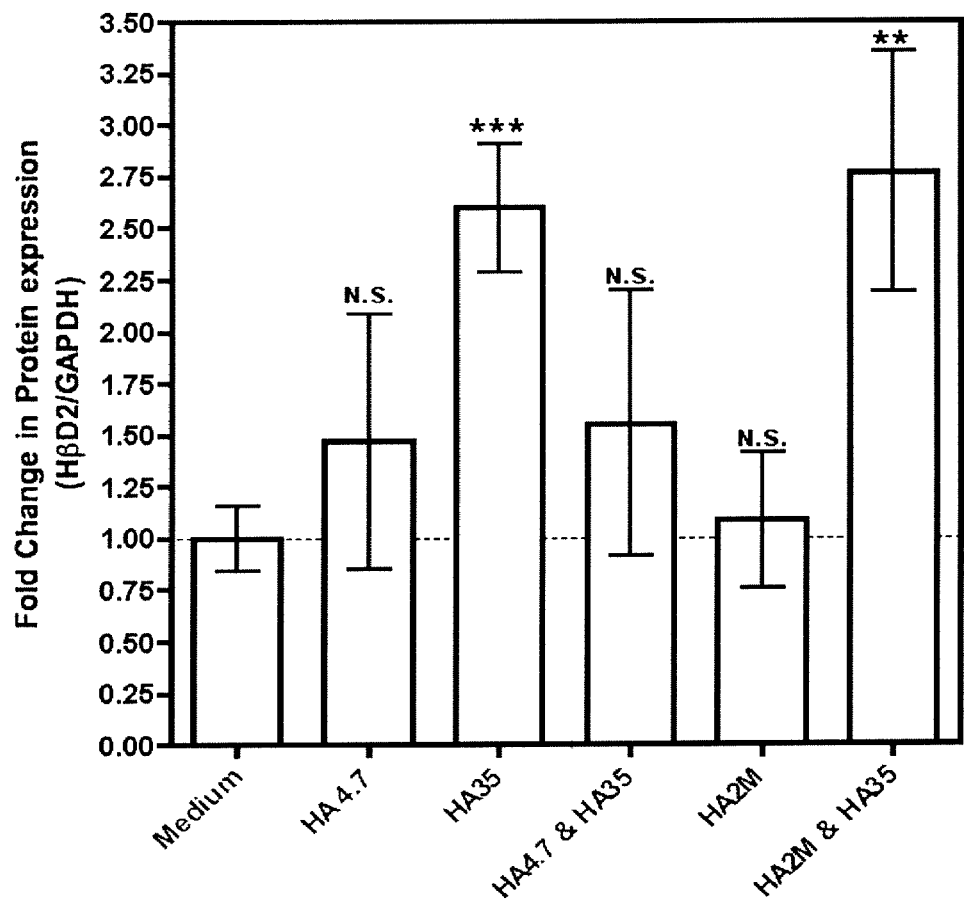
FIG. 6A is a bar graph presenting data from an experiment wherein HT29 colonic epithelial cells were contacted with 4.7 kDa, 35 kDa, 2000 kDa HA fragment preparations, individually or in mixed preparations, for 8 hours. More particularly, cells were contacted with HA4.7 (10 μM, i.e., 0.047 mg/ml); HA35 (10 μM, i.e., 0.35 mg/ml), HA2M (0.18 μM, i.e., 0.35 mg/ml) or mixtures thereof as indicated. Human beta defensin 2 (HBD2) levels were determined relative to the housekeeping protein Glyceraldehyde-3-phosphate dehydrogenase (GAPDH). Relative HBD2/GAPDH protein expression levels were determined by Western Blot analysis. The results demonstrate that 35 kDa hyaluronan sized fragments induced the greatest accumulation of HBD2, but that 4.7 kDa hyaluronan fragments inhibited the ability of HA35 to induce accumulations of HBD2.

Cell contacted with fragment-supplemented medium treatments containing HA35 showed the greatest production of human beta defensin 2 production (See FIG. 6). Cells contacted with the fragment-supplemented medium treatments containing both HA35 and HA4.7 produced less human beta defensin 2, indicating that the addition of 4.7 kDa HA and inhibited the HA-35 kDa response. However, adding 2000 kDa HA to the fragment-supplemented medium treatments containing both HA35 did not inhibit the HA-35 kDa response. This suggests that the HA-35 kDa response is mediated through a receptor that recognizes the smaller molecular weight HA (in animals the receptor is believed to be the Toll like receptor-4) and the 4.7 size is a competitor for the HA35.

We claim:

1. A method of enhancing the expression of human beta defensin 2 (HBD2) in a human patient's colon epithelium cells, said method comprising the step of orally administering a pharmaceutical composition to said patient, wherein said composition comprises hyaluronan and a pharmaceutically acceptable carrier, and said hyaluronan component consists of hyaluronan fragments having a molecular weight of about 35 kDa.

2. A method of enhancing the expression of human beta defensin 2 (HBD2) in human colon epithelium cells, said method comprising orally administering an aqueous solution comprising hyaluronan, wherein said hyaluronan component of the aqueous solution consists of hyaluronan fragments having an average molecular weight selected from a range of 30 to 45 kDa, and comprising less than 0.1% of hyaluronan fragments having a molecular weight of less than 10 kDa relative to the total detectable hyaluronan content.

3. The method of claim 2 wherein said hyaluronan fragment have an average molecular weight of 35 kDa.

4. A method of enhancing the expression of human beta defensin 2 (HBD2) in a human patient's colon epithelium cells, said method consisting of orally administering a pharmaceutical composition to said patient, wherein said composition comprises a hyaluronan component and a pharmaceutically acceptable carrier, and said hyaluronan component consists of hyaluronan fragments having a molecular weight selected from a range of about 30 to about 45 kDa.

5. The method of claim 4 wherein the pharmaceutical composition consists of hyaluronan fragments having a molecular weight of about 35 kDa and a pharmaceutically acceptable carrier.

* * * * *